(12) United States Patent
Gabbay

(10) Patent No.: US 6,572,627 B2
(45) Date of Patent: Jun. 3, 2003

(54) SYSTEM TO INHIBIT AND/OR CONTROL EXPANSION OF ANATOMICAL FEATURES

(76) Inventor: Shlomo Gabbay, #1 Randall Dr., Short Hills, NJ (US) 07078

(*) Notice: Subject to any disclaimer, the term of this patent is extended or adjusted under 35 U.S.C. 154(b) by 180 days.

(21) Appl. No.: 09/756,065

(22) Filed: Jan. 8, 2001

(65) Prior Publication Data

US 2002/0091395 A1 Jul. 11, 2002

(51) Int. Cl.$^7$ .............................................. A61B 17/00
(52) U.S. Cl. ........................................ 606/151; 606/157
(58) Field of Search .............................. 600/37; 606/139, 606/140, 142, 151, 157, 158, 213; 128/899

(56) References Cited

U.S. PATENT DOCUMENTS

| | | |
|---|---|---|
| 3,972,469 A | 8/1976 | Wright |
| 4,403,604 A * | 9/1983 | Wilkinson et al. ............ 600/37 |
| 4,592,339 A * | 6/1986 | Kuzmak et al. ............ 128/899 |
| 4,632,114 A | 12/1986 | Todd et al. |
| 5,074,868 A * | 12/1991 | Kuzmak ..................... 604/909 |
| 5,160,338 A * | 11/1992 | Vincent ........................ 600/3 |
| 5,330,451 A | 7/1994 | Gabbay ...................... 604/284 |
| 5,449,368 A * | 9/1995 | Kuzmak ..................... 604/909 |
| 5,549,621 A * | 8/1996 | Bessler et al. .............. 227/902 |
| 5,599,329 A | 2/1997 | Gabbay ...................... 604/284 |
| 6,102,922 A | 8/2000 | Jakobsson et al. .......... 606/157 |
| 6,375,608 B1 * | 4/2002 | Alferness ..................... 600/37 |

OTHER PUBLICATIONS

"Surgical Treatment for Morbid Obesity", by JEG Bariatric Services Group, from Website www.jegweightloss.com (date unknown).

Goldberg, S., et al. "Vertical Banded Gastroplasty: A Treatment for Morbid Obesity". vol. 72. No. 6. pp. 988, 991–1003. Aorn Jornal. Dec. 2000.

PCT International Search Report—Date of Mailing Jun. 21, 2002.

* cited by examiner

Primary Examiner—Danny Worrell
(74) Attorney, Agent, or Firm—Tarolli, Sundheim, Covell & Tummino L.L.P.

(57) ABSTRACT

A system according to the present invention helps to reduce consumption of food by a patient. In one aspect, the system includes a banding apparatus which may be applied to around part of a patient's stomach to reduce that part to a reduced diameter. Another aspect provides wrapping apparatus that may extend from the banding apparatus and around an upper pouch of the stomach to inhibit expansion of the upper pouch beyond a predetermined volume. The wrapping apparatus further may be anchored relative to part of the patient's body to mitigate diaphragmatic hernia.

32 Claims, 4 Drawing Sheets

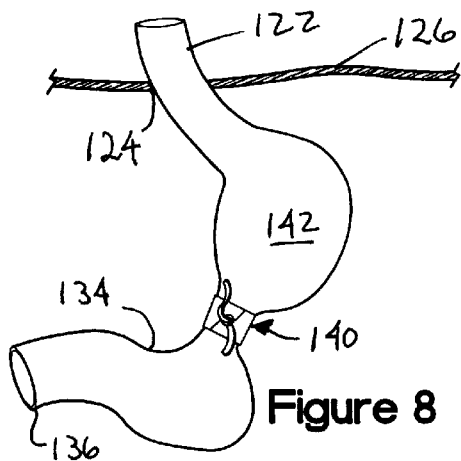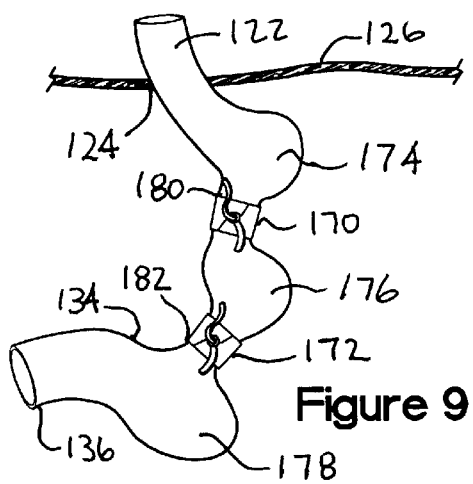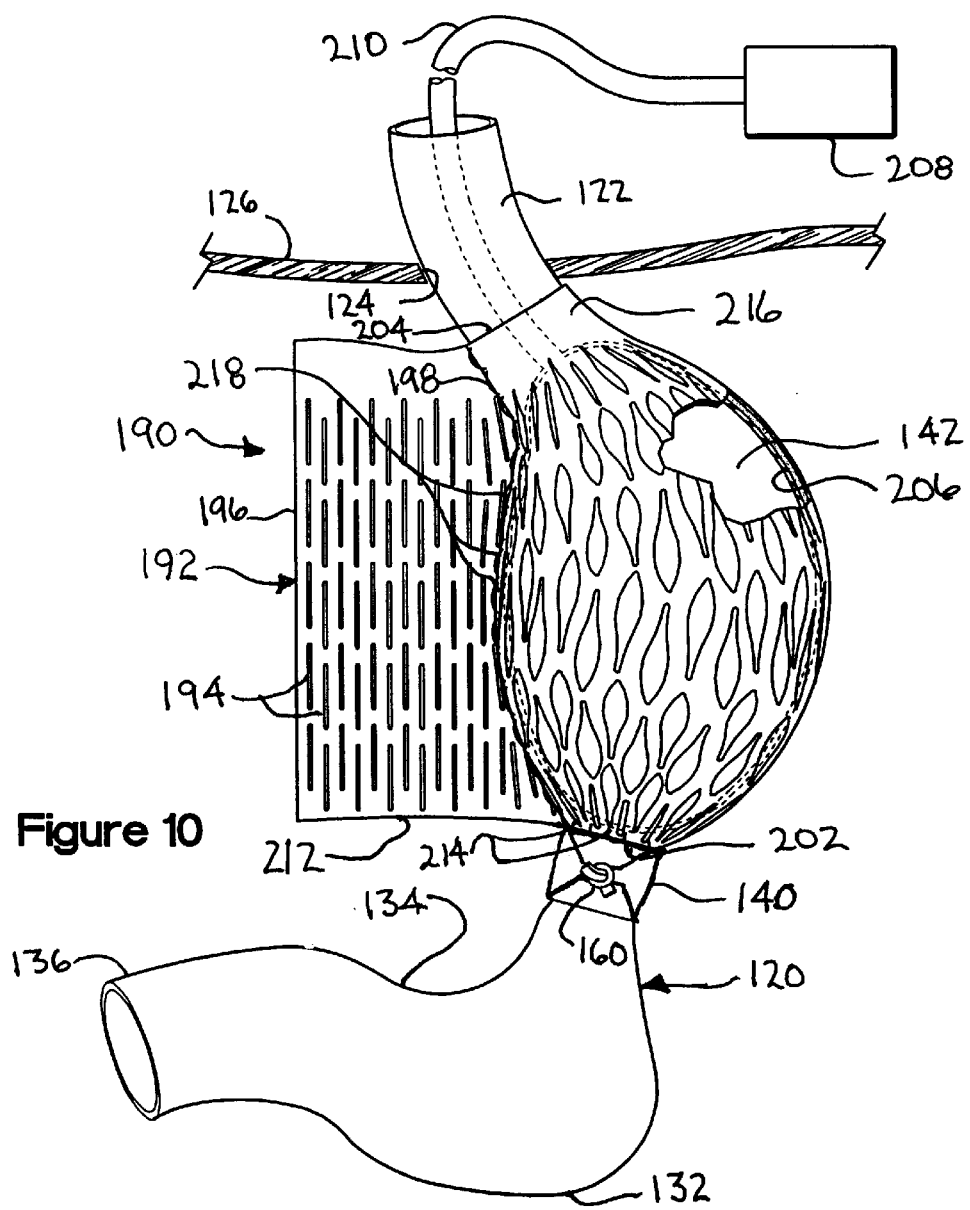

SYSTEM TO INHIBIT AND/OR CONTROL EXPANSION OF ANATOMICAL FEATURES

TECHNICAL FIELD

The present invention relates to weight control and, more particularly, to a system and method to inhibit gastric expansion.

BACKGROUND

Obesity in adults and children has been dramatically increasing in the United States and abroad. Of particular interest is morbid obesity. Obesity typically is determined based on a body mass index (BMI), which is a ratio of weight and height. In general, a BMI of 30 or greater is considered obese and a BMI of 40 or greater is considered morbidly obese.

Obesity can be associated with several detrimental physiological conditions. For example, obesity often makes it difficult to breathe (e.g., sleep apnea) and may cause severe shortness of breath. Obese women may further have irregular menstruation patterns. More serious conditions, such as gallbladder disease, hypertension, diabetes, and high blood pressure, also may accompany obesity. Physical conditions also may develop as a result of obesity, such as osteoarthritis at various joints that are subject to increased stress due to the obese condition. An Obese person also may suffer from various social and psychological effects due to their condition.

In an effort to reduce the occurrence of obesity, several surgical procedures have been developed in situations when dieting alone is inadequate. One type of procedure, commonly called gastric banding, is implemented by placing a band around the stomach to restrict its expansion and thereby reduce the consumption of food. In order to provide a means to adjust the diameter of the banding, a band was developed having an inflatable balloon on the inside thereof, similar to a blood pressure cuff. The balloon could be connected to an injection port, which could be used to adjust inside diameter of the band postoperatively. As a result, the restriction around the stomach could be modified according to the needs of an individual patient.

However, such gastric banding techniques have not been completely satisfactory. For example, conventional bands have a tendency to dislocate and travel downwards towards the lower part of the stomach. In addition, it has been determined that the upper part of the stomach above the band tends to rapidly increase in size. For example, an upper gastric pouch formed by the banding may increase up to ten times its original volume, facilitating increased food consumption and less weight reduction.

Another more invasive surgical method is gastric bypass in which the stomach is stapled vertically to create a small vertically oriented pouch for food intake. A lower part of the stomach and a varying amount of the small intestine is bypassed. Gastric bypass is usually a permanent procedure and can lead to serious complications, such as anemia, poor nutrient absorption. In addition, there is an increased difficulty to evaluate the gastrointestinal tract, as a substantial portion of it is blocked by staples. A dumping syndrome also may occur with gastric bypass, which may include symptoms of flushing, abdominal pain, and diarrhea after rapid emptying of food into the jejunum.

Vertical banded gastroplasty (VBG) is an alternative to gastric bypass in which a surgeon makes a circular window through the stomach a few inches below the esophagus. Stapling from the window to the esophagus creates a small vertical pouch. A band of polypropylene is inserted through the window and around the outlet of the pouch and sutured to itself to form a closed band loop. While VBG mitigates the complications cause by bypassing the stomach and part of the small intestine, other problems still exist. For example, there is an increased risk of re-operation due to the patient tearing the suture line. In addition, the patient's stomach pouch may become obstructed unless food is chewed sufficiently and large pills are crushed prior to consumption.

While such surgical procedures may initially reduce the size of the stomach and, thereby reduce consumption, such procedures are not without risks and complications, as noted above.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

One aspect of the present invention provides a system and method to inhibit radial expansion the stomach. The system includes an elongated band (or patch) of a flexible biocompatible material. In accordance with a particular aspect, the material may be formed of a natural tissue material, such as animal pericardium that has been fixed in a suitable fixation solution. The band has a central body portion and elongated end portions extending longitudinally from opposed ends of the body portion. The end portions have a width that is less than the body portion.

A slot is formed through an intermediate portion of the body portion. The slot is adapted to receive one of the end portions there through. In particular, part of the central body portion located intermediate the slot and one of the end portions has a width that approximates or is slightly less than the length of the slot. Accordingly, the banding system may be wrapped around a desired part of an organ (e.g., the stomach) and an end portion may be inserted through the slot and the two opposed end portions urged apart to form a cylindrical body member of the central body portion having a desired diameter. Next, the end portions may be tied off (or otherwise secured) so that the cylindrical member maintains at least the desired diameter.

In accordance with another aspect of the present invention, a wrapping system may be used in conjunction with a banding apparatus to further limit dilation of part of an organ, such as the stomach. The wrapping system includes a sheet of a flexible biocompatible material dimensioned and configured to have a sufficient surface area to wrap around the part of the organ. A plurality of slots or apertures extend through the sheet at spaced apart locations in a substantial portion of the sheet. The slots or apertures operate to permit a limited amount of expansion of the sheet. In accordance with a particular aspect of the present invention, the sheet is formed of a biocompatible natural tissue material, such as, for example, treated animal pericardium.

To utilize the wrapping system in combination with a banding apparatus, the wrapping system is applied circumferentially around the desired part of the organ with one end being positioned adjacent the banding system. In order to selectively limit the amount of expansion of the organ, an inflatable balloon or bladder may be inserted within the organ and inflated to approximate a desired maximum volume thereof. Then, by applying the sheet about the inflated organ in a substantially tight condition, and securing the wrapping about the organ, expansion of the organ will be limited to about that volume. The end of the wrapping system may, in turn, be attached to the banding system, so as to inhibit axial movement of the applied banding system relative to the organ.

According to another aspect of the present invention, the wrapping system may be employed, with or without the banding, to inhibit diaphragmatic hernia. The wrapping system may be applied around a portion of the stomach adjacent the esophagus with one end of the wrapping system being applied so as to circumscribe the esophagus. A distal portion of the wrapping system in turn is applied around the stomach and sutured together to form a cylindrical around at least part of the stomach. An anchor of a biocompatible material is attached to the wrapping system and to an adjacent internal body part, such as the abdominal wall or the diaphragm at a location distal the esophageal hiatus. As a result, the wrapping system and the upper portion of the stomach within the wrapping system are inhibited from herniating through the esophageal hiatus.

BRIEF DESCRIPTION OF THE DRAWINGS

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings, in which:

FIG. 8 illustrates the banding apparatus applied to the stomach in accordance with the present invention;

FIG. 9 illustrates more than one banding apparatus applied to a stomach in accordance with the present invention;

FIG. 10 is an example of a wrapping apparatus being applied around a stomach in accordance with the present invention;

DESCRIPTION OF THE INVENTION

Figure 1:
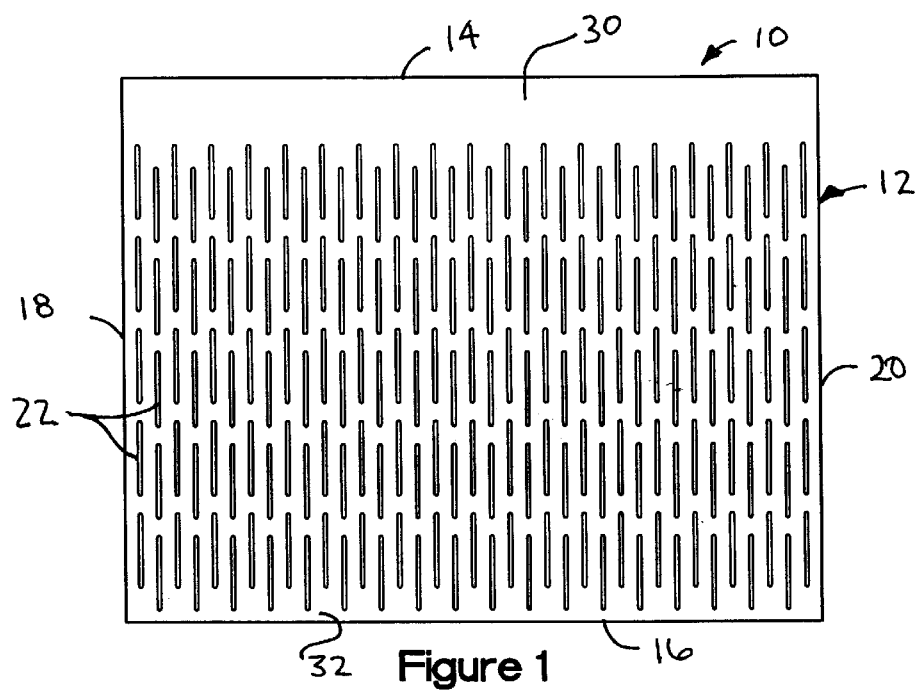
FIG. 1 is an example of a wrapping apparatus in accordance with the present invention.

FIG. 1 is an example of a wrapping apparatus 10 in accordance with an aspect of the present invention. The wrapping apparatus 10 is formed of a generally flexible sheet 12 of biocompatible material. The sheet 12 has end portions 14 and 16 spaced apart from each other by elongated side edges 18 and 20 extending between the ends thereof. The sheet is dimensioned and configured to have a surface area sufficient to enclose a volume of a desired size and shape, namely part of a stomach.

The sheet includes a plurality of apertures 22 formed through the sheet 12 extending from one surface of the sheet to the opposite surface of the sheet. The apertures 22 are disposed about the sheet 12 at numerous spaced apart locations thereof. In this example, the apertures 22 are illustrated as elongated slots extending in a direction between the ends. It is to be appreciated by those skilled in the art that such apertures also could extend in other directions or in more than one direction as well as have a configuration or relative size different from that shown.

A portion 30 of the sheet 12 extending between the edges 18 and 20 at the end 14 includes no apertures. Another portion 32 of the sheet 12 at the other end 16 also has no apertures. In this example, the width of the portion 32 is less than the width of the portion 30. The absence of apertures at such portions 30 and 32 generally inhibits expansion of such portions.

Figure 2:
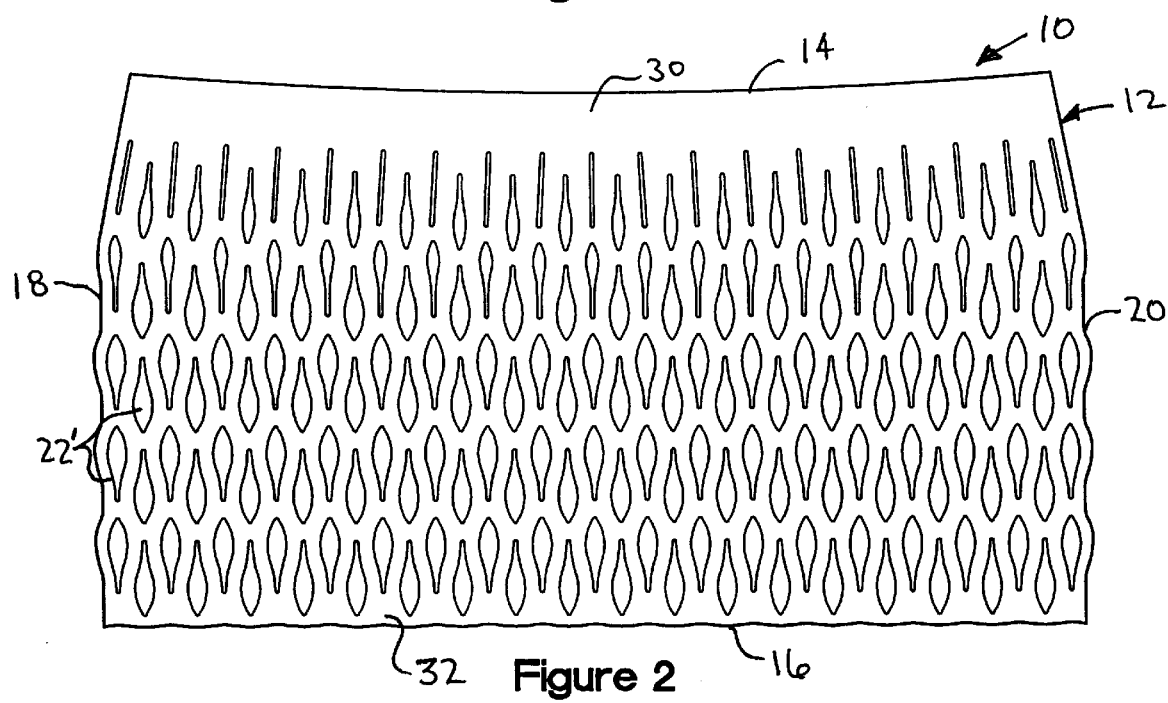
FIG. 2 is an example of the wrapping apparatus illustrated in a stretched condition.

In contrast, the portion of the sheet 12 having the plurality of apertures 22 intermediate the portions 30 and 32 facilitates expansion of the sheet to the extent permitted by the dimensions and configurations of the apertures. FIG. 2, illustrates the sheet of FIG. 1 in an expanded condition, such as due to urging the side edges 18 and 20 apart. The apertures, indicated at 22', are in an expanded condition, thereby enable lateral expansion of the sheet 12. Those skilled in the art will understand and appreciate that the amount of expansion of the sheet 12 may be controlled as a function of the size and configuration of the apertures.

In accordance with an aspect of the present invention, the sheet 16 is formed of a natural tissue biocompatible, such as animal pericardium (e.g., bovine, equine, porcine, etc.). The natural tissue sheet 12 may be chemically treated in a suitable fixation solution, such as glutaraldehyde. By way of further illustration, the sheet 12 may be formed from a sufficiently large NO-REACT® patch, which is commercially available from Shelhigh, Inc., of Millburn, N.J. The NO-REACT® patch helps improve the biocompatibility of the resulting wrapping system 10, thereby mitigating the likelihood of a patient rejecting an implanted system. The NO-REACT® pericardial patch also resists calcification. It is to be understood and appreciated that other types of biocompatible materials (e.g., natural or synthetic) also could be utilized to form a wrapping system 10 in accordance with the present invention.

Figure 3:
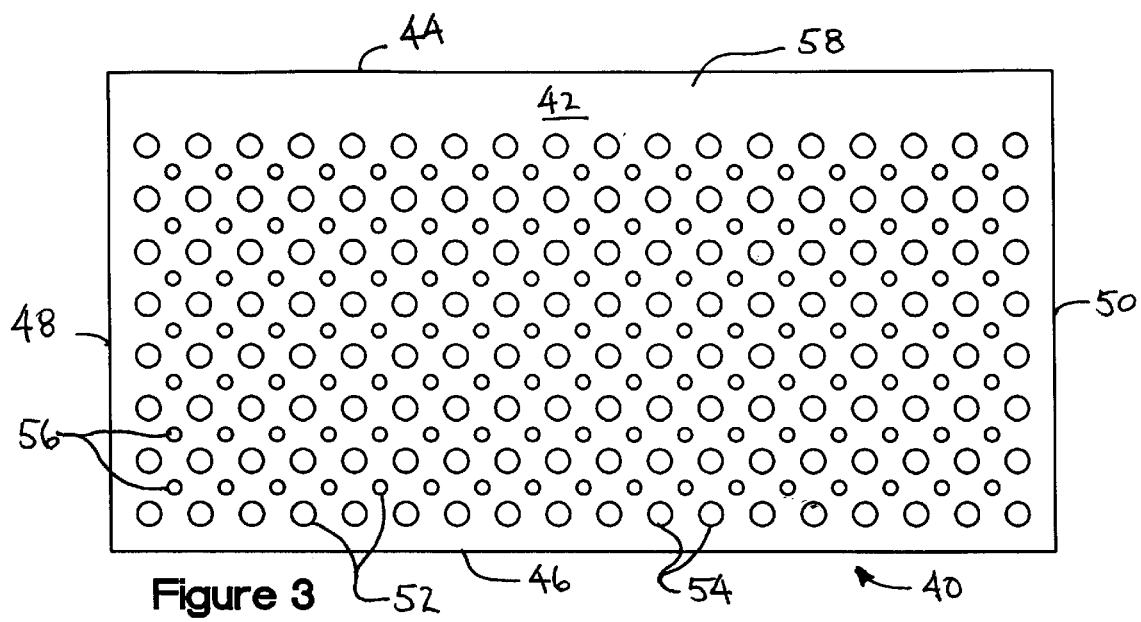
FIG. 3 is an example of another wrapping apparatus in accordance with the present invention.

FIG. 3 illustrates another example of a wrapping system 40 in accordance with an aspect of the present invention. The wrapping system 40 includes a sheet 42 of flexible biocompatible material, which may be substantially similar to the material described above with respect to FIGS. 1 and 2. The sheet 42 has ends 44 and 46 that are spaced apart from each other by side edges 48 and 50 of the sheet. Numerous apertures 52 are formed through the sheet 12 at spaced apart locations. In this particular example, generally circular apertures of different sizes, indicated at 54 and 56, are formed through the sheet.

While the apertures 52 are illustrated as being generally circular, it is to be appreciated that the shape of the apertures are not limited to a circular configuration. For example, elliptical, rectangular, polygonal, teardrop, and other shapes also could be used in accordance with an aspect of the present invention. Similar to the sheet of FIGS. 1 and 2, this sheet has a portion 58 at the end 44 and another portion 60 at the other end 46, which portions have no apertures. The width of the portion 60 may be less than the width of the other portion 58.

Figure 4:
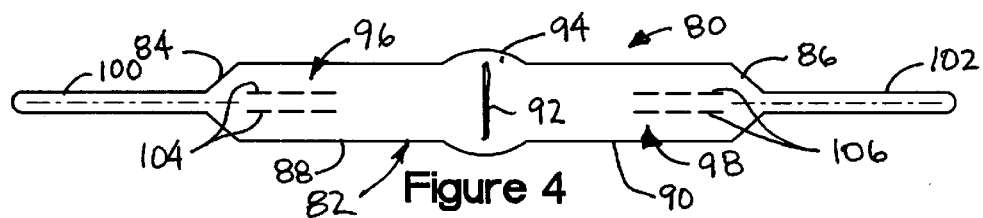
FIG. 4 is an example of a banding apparatus in accordance with the present invention.

FIG. 4 illustrates a banding apparatus 80 in accordance with an aspect of the present invention. The banding apparatus 80 includes an elongated body portion 82 having ends 84 and 86 spaced apart by elongated side edges 88 and 90. An elongated slot 92 extends through a central region 94 of the body 82 intermediate the ends 84 and 86 thereof. The slot 92 extends from a location near one side edge 88 to a location near the other side edge 90. In this example, the central region 94 of the body 82 is slightly bulbous proximal the slot 92.

By way of example, the slot 92 operates to divide the body 82 into two parts 96 and 98. One part 96 has a width between its side edges 88 and 90 that is slightly less than the width between the side edges of the other part 98 of the body 82. In particular, the width of the part 96 approximates or is slightly less than the length of the slot 92 so as to facilitate movement of the body part through the slot.

Elongated end portions 100 and 102 extend generally axially from respective ends 84 and 86 of the body 82. Each elongated end portion 100 and 102 has a width that is less than the width of its associated body part 96 and 98 from which it extends.

A plurality of perforations or small slots 104 and 106 are formed through each body portion 96 and 98, respectively, at a location adjacent the respective ends 84 and 86. Each set of slots 104, 106 are arranged as pairs of substantially parallel perforations spaced apart a distance commensurate with the width of the adjacent end portion 100, 102. The perforations 104 and 106 provide a convenient means to decrease the length of the body part 96 and 98 through which they extend.

For example, a surgeon may cut from an end 84, 86 through the adjacent perforations 104, 106 so as to remove part of the associated body 96, 98. As a result, the length the associated end portion 100, 102 may be increased accordingly.

While three such sets of perforations 104 and 106 are illustrated in FIG. 4, it is to be understood and appreciated by those skilled in the art that other numbers of perforations could be utilized in accordance with an aspect of the present invention. As an alternative to such perforations, 104 and 106, a surgeon may cut axially through a desired length of the body portion to remove it to elongate the associated end portion and reduce the length of the body 82. It may be desirable to reduce the length of the body portion, for example, in order to reduce the resulting diameter of the banding when applied to a patient's organ. A smaller diameter banding, as applied, further inhibits food consumption by the patient.

In accordance with an aspect of the present invention, the banding apparatus 80 is formed of a flexible natural tissue material, such as animal pericardium (e.g., bovine, equine, porcine, etc.). For example, the banding apparatus 80 may be formed from a rectangular sheet of a NO-REACT® pericardial patch, similar to the wrapping systems described hereinabove.

In view of the foregoing examples of different structures, exemplary methodologies and uses of such structures will be better appreciated with reference to the figures described below in which like reference characters refer to similar parts throughout the various views. It will be understood and appreciated by those skilled in the art that such examples are meant to illustrative of possible uses, as such structures may be utilized in other ways, which are contemplated as falling within the scope of the present invention.

Figure 5:
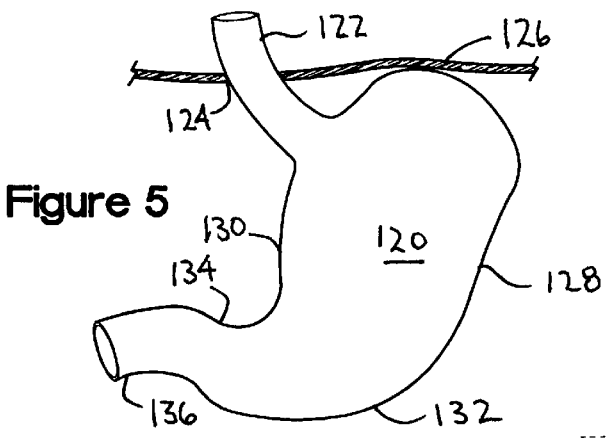
FIG. 5 is a partial view of an abdomen, illustrating part of the gastro-intestinal tract.

FIG. 5 is internal view of part of an abdomen showing a stomach 120. An esophagus 122 extends through an esophageal hiatus 124 of the diaphragm 126. The stomach 120 has greater and lesser curvatures 128 and 130, respectively, and a fundus 132 located near a lower portion. The stomach 120 terminates at a pylorus 134, which leads to the small intestine 136. In response to consumption of food, the stomach 120 may expand to many times its normal size to accommodate such consumption. In morbidly obese persons, the stomach 120 may reach a volume several times its normal size, which requires enormous intake of food for satiety to occur.

Figure 6:
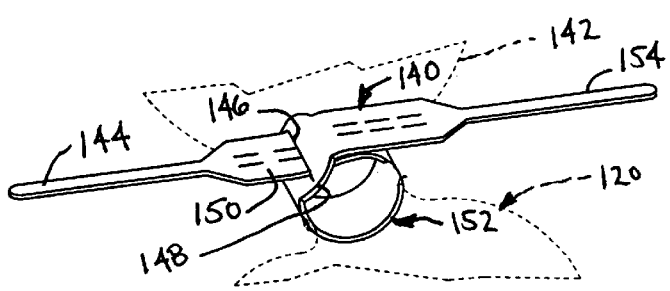
FIG. 6 is an example of a banding apparatus being applied to a stomach in accordance with the present invention.

FIG. 6 illustrates a banding apparatus 140 being applied around a portion of the stomach 120 in accordance with an aspect of the present invention. The banding may be substantially identical to that described above with respect to FIG. 4.

In this example, the banding 140 is applied around an intermediate part of the stomach 120 just above the fundus. It is to be appreciated that the banding 140 could be placed at any location as deemed appropriate by the surgeon to compartmentalize the stomach 120, so as to create a desired size pouch 142 between the banding and the esophagus (see, e.g., FIG. 5).

At this particular stage, an end portion 144 of the banding apparatus 140 has been inserted through an intermediate slot 146 located in a central region of the body 148 of the banding. The end portion 144 has been pulled through the slot 146, such that part 150 of the central body portion 148 also extends through the slot. As mentioned above, one part (or both parts) 150 of the body portion has a width that approximates or is slightly less than the slot length so as to facilitate its insertion through the slot 146. The body 148 of the banding apparatus 140 that circumscribes the stomach 120 forms a generally cylindrical portion, indicated at 152. The two ends 144 and 154 of the banding apparatus 140 thus may be urged apart from each other in substantially opposite directions to reduce the diameter of the cylindrical portion 152 and, in turn, the part of the stomach 120 enclosed by the cylindrical of the body 148.

Figure 7:
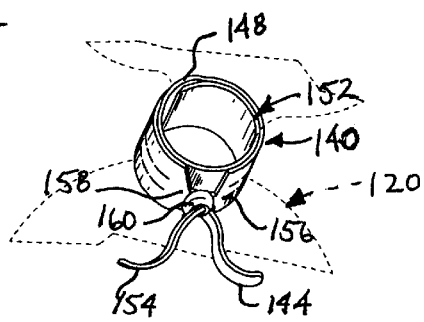
FIG. 7 illustrates another part of the banding application process in accordance with the present invention.

FIGS. 7 and 8 illustrate the banding apparatus 140 being secured relative the stomach 120 in accordance with an aspect of the present invention. The cylindrical portion 152 has been reduced to a desired diameter, with the ends 144 and 154 being tied together in a knot to maintain its diameter around the stomach 120. In particular, ends 156 and 158 of the body portion 148 are urged toward each other, such as by tying the elongated end portions together in a knot 160, illustrated in FIG. 7.

As shown and described with respect to FIG. 4, the length of the body portion 148 may be modified prior to being applied around the stomach 120 by cutting from one or both ends 156, 158 of the body (e.g., through perforations) to extend the length of its respective end portion 154, 144. While the banding apparatus 140 illustrated in FIGS. 7 and 8 is attached to the stomach 120 by tying its end portions 144 and 154 in a knot 160, those skilled in the art will understand that, in addition or as an alternative to tying such ends in a knot, the banding could be secured relative to the stomach by other means, such as sutures or surgical staples.

As a result of the banding apparatus 140, the stomach 120 has a reduced diameter at a selected location between the pylorus 134 and the esophagus 122. The restricted diameter helps reduce food consumption. For example, as the pouch 142 formed between the banding 140 and the esophagus 122 fills with food, such food travels through the restricted portion of the stomach at a reduced rate so that the pouch fills more quickly. This, in turn, creates a feeling of satiety, such that overall food consumption may be reduced. Those skilled in the art will understand and appreciate that the banding apparatus 140 could be selectively located at other positions on the stomach 120 and have a selected diameter to help control food consumption in a desired manner.

FIG. 9 illustrates an example in which two banding apparatuses 170 and 172, in accordance with an aspect of the present invention, have been applied to the stomach. This arrangement divides the stomach into two separate pouches 174 and 176 and the remaining part of the stomach 178. The arrangement further provides two portions of the stomach having reduced and restricted diameters, indicated at 180 and 182, to help inhibit the rate at which food may be consumed. The first pouch 174 between the first banding apparatus 174 and esophagus 122 operates similarly to the banding of FIG. 8, namely, by filling with food more quickly than would the entire stomach 120 in the absence of the banding. The restriction of the stomach caused by the banding inhibits the flow of food from the first pouch 174 to the second pouch 176.

The subsequent restriction 182 of the stomach 120 further reduces the rate at which food may travel from the second pouch 176 to the remaining part of the stomach 178. Because food tends to remain in the second pouch 178 for a greater than usual time, the flow of food from the first pouch to the second pouch is further reduced. Consequently, the multiple bandings help curb consumption to a greater extent than a single banding apparatus, as shown in FIG. 8.

Referring back to FIG. 8, for example, it is possible that the pouch 142 formed between the banding 144 and the esophagus 122 may, upon increased consumption, expand to an increased volume. The increase volume, for example, can approach several times (e.g., up to ten times) its initial size. Consequently, the desired benefits from gastric banding, such as the approach described above as well as other types of gastric banding, may be temporary. Therefore, it is desirable to provide a way to inhibit the natural expansion of the stomach from occurring in situations when gastric banding is employed.

FIG. 10 illustrates part of a procedure in which a wrapping system 190 (see, e.g., FIGS. 1–3) is utilized in conjunction with a banding apparatus 144 in accordance with an aspect of the present invention. In particular, the banding apparatus 144 has been already been applied to the stomach 120, such as shown and described with respect to FIGS. 6–8. The wrapping 190 is formed of sheet of material 192 having a plurality of apertures 194, such as described above with respect to FIGS. 1–3.

The sheet 192 has side edges 196 and 198 that are wrapped around the pouch 142 to enclose the pouch. One end 202 of the sheet 192 is positioned around the stomach 120 adjacent the banding 144. The other end 204 of the sheet 192 is applied around the esophagus 122 that extends through the esophageal hiatus 124. Because the wrapping 190, in accordance with an aspect of the present invention, is intended to limit the volume to which the pouch 142 formed between banding 144 and the esophagus 122 can expand, it is helpful if the pouch is expanded to about such size as the wrapping is applied.

For example, an inflatable bladder or balloon 206 may be inserted through the esophagus 122 into the pouch 142 of the stomach 120 intermediate the banding 144 and esophagus. A source of inflation fluid (e.g., air, saline solution, water, etc.), indicated schematically at 208, is in fluid communication with the bladder 206 through a tube 210. The source 208 may be employed to inflate the bladder 206 to the desired volume. The sheet 192 may then be applied around the expanded pouch. In particular, the sheet 192 may be stretched generally tight around the inflated pouch 142, as shown in FIG. 10. As a result of stretching the sheet 192 around the inflated pouch, the sheet is applied in its expanded condition (e.g., FIG. 2) so as to limit additional expansion of the pouch 142 beyond such volume. Excess length 212 of the wrapping of the sheet proximal the loose end 196 may be trimmed.

Figure 11:
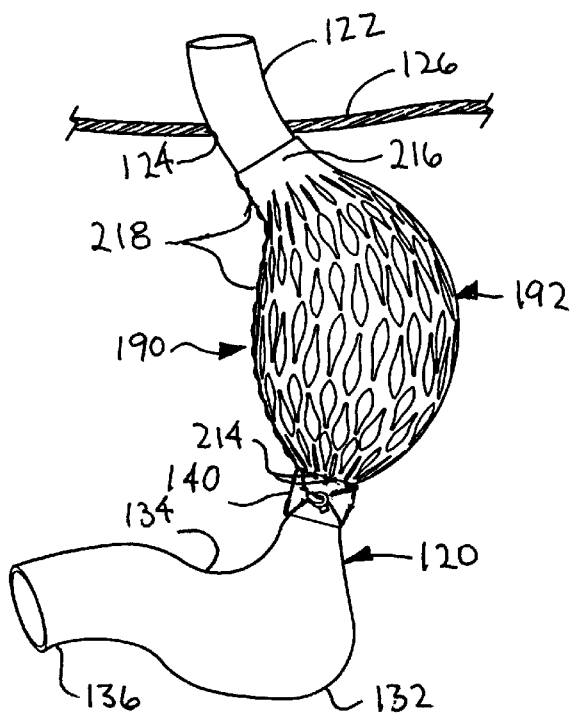
FIG. 11 illustrates a completed banding/wrapping procedure in accordance with an aspect of the present invention.

As shown in FIGS. 10 and 11, the end 202 of the sheet 192 is secured to an adjacent end of the banding apparatus 144, such as by sutures 214. The other end 204 is also secured around the esophagus 122. In a particular aspect, an end portion 216 of the sheet 192 having little or no apertures is applied around the esophagus 122 so as to have a restricted diameter that is substantially less than that of the expanded pouch 142, but that approximates the esophagus.

The side edge 198 of the sheet further is secured to a corresponding part of the sheet 192, so as to enclose the pouch in its expanded condition to a desired volume. For example, sutures 218 may be applied to connect the side edge 198 of the sheet 192 around the pouch 142 to an intermediate part of the sheet. Such suturing may occur before or after the volume of the pouch 142 has been reduced to by removing fluid from the bladder 206.

As a result, the banding apparatus 144 and the esophageal end portion 216 form spaced apart ends of the 190 to help reduce food consumption. The ends of such system have generally fixed diameters, which may be substantially equal (e.g., about one inch or less), capable of little (if any) expansion. The intermediate portion of the sheet 192 having the apertures permitting expansion and contraction between a reduced volume and the expanded volume. The expanded volume condition approximates the volume to which the enclosed pouch 142 was inflated during the procedure (FIG. 10). Thus, as the stomach 120 expands due to food consumption, the stomach generally can expand to only about such expanded volume. In addition, the banding apparatus 144 and the opposed end of the wrapping system operate to hold the system 192 in place on the stomach, thereby mitigating movement of system.

Figure 12:
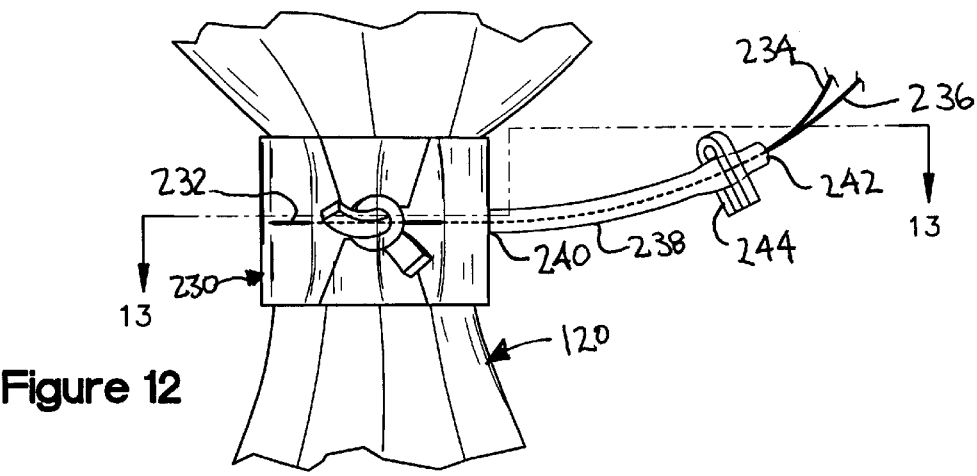
FIG. 12 illustrates an enlarged view of part of the banding/wrapping system of FIG. 11, illustrating a system to restrict the diameter of the banding portion thereof in accordance with the present invention.
Figure 13:
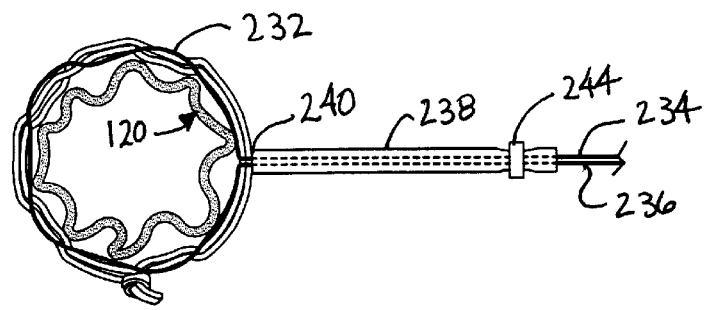
FIG. 13 is partial sectional view showing the restriction system associated with the banding of FIG. 12.

FIGS. 12 and 13 illustrate another aspect of a banding system 230 in accordance with an aspect of the present invention, which is operative to modify the diameter of the banding. The banding system 230, for example, is applied around part of a stomach 120 in a substantially similar manner to that shown described herein, although other banding arrangements also could incorporate the restriction mechanism in accordance with the present invention. A purse string suture 232 (e.g., a relatively thick monofilament) is applied circumferentially around and through the banding 230, such as shown in FIGS. 12 and 13. The purse string 232 is operable to reduce the diameter of the banding 230 around the stomach 120 to less than the original diameter of the banding.

For example, two ends 234 and 236 of the purse string suture extend from the banding through an elongated conduit 238, such as a silicon rubber tube or other biocompatible tube (e.g., having a diameter of about 1/8 inches). The conduit 238 has a first end 240 at a location engaging the banding 230 and a distal end 242 spaced apart from the first end. A clip (or other retaining mechanism) 244 may be applied near the distal end 242 of the conduit 238 to clamp the sutures 234 and 236 within the conduit and in turn prevent their continued movement through the conduit. Because, the clip 244 fixes the sutures 234 and 236 relative the conduit, the diameter of the banding 230 is also fixed to a diameter according to the length of the sutures 232 extending from the end 240 of the conduit 238.

In accordance with an aspect of the present invention, the diameter of the banding 230 may be modified by adjusting the length of the sutures 232 extending from the conduit 238. For example, the distal end 242 of the conduit 238 may extend from the stomach through the abdominal wall and terminate at (or near) a location accessible from outside the patient's body postoperatively. The conduit 238 is sufficiently stiff such that the ends of the sutures 234 and 236 may be pulled through the conduit relative the banding. This reduces the length of the suture extending from the proximal end 240 of the conduit and, in turn, reduces the diameter of the banding 230. Advantageously, a surgeon may reduce the diameter of the banding 230, in accordance with an aspect of the present invention, such as if the patient does not sufficiently reduce food consumption after receiving either a gastric banding (e.g., FIGS. 8 or 9) or a banding-wrapping system (e.g., FIG. 11) incorporating the adjustment mechanism shown and describe in FIGS. 12 and 13. It will be appreciated that the additional restriction of the stomach (e.g., by reducing the diameter of the banding) does not require additional surgery.

Figure 14:
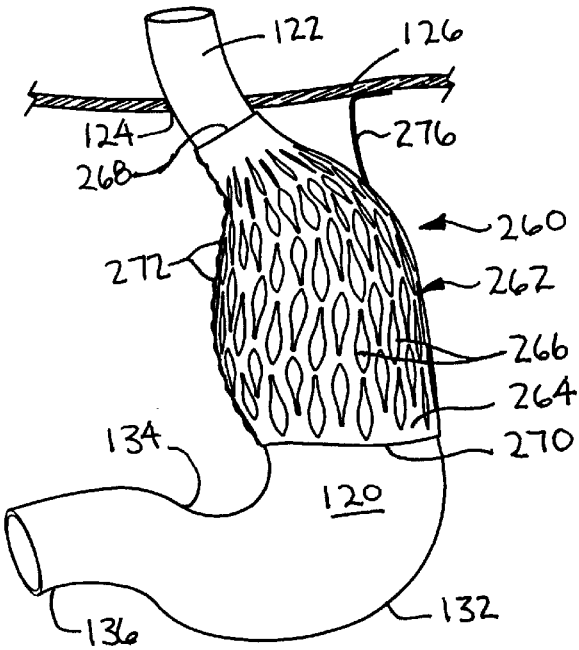
FIG. 14 is an example of a wrapping apparatus applied to a stomach to inhibit diaphragmatic hernia of the stomach.

FIG. 14 illustrates a system 260 employed to inhibit diaphragmatic hernia in accordance with an aspect of the present invention. The system 260 includes a wrapping apparatus 262 that is substantially similar to that shown and described with respect to FIGS. 1–3 and 10. Briefly stated, the wrapping apparatus 262 includes a sheet 264 of a flexible, biocompatible material having a plurality of apertures 266 formed through the sheet at numerous spaced apart locations. The sheet 264 has ends 268 and 270 spaced apart from each other by side edges of the sheet.

In this example, the sheet 264 has been wrapped around an upper part of the stomach 120, with the end 268 enclosing part of the esophagus 122. Side edges and of the sheet 264 further are secured together, such as by sutures 272 along a seam formed by adjoining edges.

In accordance with the present invention, a length of a biocompatible material 276 connects the wrapping apparatus 262 to part of the patient's body distal the esophageal hiatus 124 to inhibit the stomach 120 from herniating through the hiatus. The length of material 276, for example, may be a strip or patch of a natural tissue material, such as treated animal pericardium. Such a strip may be secured by sutures to the wrapping apparatus 262 and to part of the patient's body distal the hiatus 124. In the example illustrated in FIG. 14, the length of material 276 is secured to part of the diaphragm 126, although those skilled in the art will understand and appreciate that the material alternatively (or additionally) could be secured to other parts of the patient's body (e.g., abdominal wall) in accordance with an aspect of the present invention. In addition, other materials or configurations of anchoring material (or a plurality of anchors) may be employed to inhibit movement of the enclosed part of the What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. An implantable system to inhibit expansion of an anatomical object located within the system, comprising:
   an elongated body portion of a flexible, biocompatible material having longitudinally spaced apart ends and side edges extending between the ends thereof, a slot extending a length through part of the body portion substantially transverse to a long axis of the body portion that at least approximates a width of part of the body portion proximal one of the ends; and
   first and second elongated end portions, each extending longitudinally from a respective end of the body portion, each of the elongated end portions having a width that is less than the width of the part of the body portion from which it extends;
   whereby, upon insertion of one of the first and second ends into the slot and movement of the inserted end portion through the slot and securing the end portions relative to an intermediate portion of the system, a generally cylindrical member is formed that inhibits radial expansion of the system.

2. The system of claim 1, further comprising a plurality of perforations formed through part of the body portion adjacent at least a first end thereof to facilitate reducing the length of the part of the body portion through which the perforations extend.

3. The system of claim 1, wherein the system provides a generally cylindrical member that inhibits generally radial expansion thereof in response to inserting one of the first and second end portions into the slot and urging the inserted end portion through the slot and securing the end portions relative to part of the system located between the end portions.

4. The system of claim 3, further comprising an adjustable restriction apparatus operatively associated with the cylindrical member, the restriction apparatus being operative to selectively adjust the diameter of the cylindrical member.

5. The system of claim 4, wherein the restriction apparatus further comprises at least one suture applied circumferentially about the cylindrical member to form a purse string having end portions that extend from the cylindrical member through an elongated conduit, the conduit having a first end adjacent the cylindrical member and a distal end spaced therefrom, such that the diameter of the cylindrical member may be modified by adjusting the length of the at least one suture extending from the first end of the conduit.

6. The system of claim 5, further comprising a retaining device which is operative to restrict movement of the end portions of the purse string through the conduit.

7. The system of claim 1, further comprising a sheet of a flexible biocompatible material having ends spaced apart from each other by a generally cylindrical sidewall extending between the ends of the sheet, a plurality of apertures extending through a substantial portion of the sheet at numerous spaced apart locations between the side edges of the sheet, the slots facilitating a limited amount of expansion of the sheet, one end of the sidewall being attached to and extending from a side edge of the body portion.

8. The system of claim 7, further comprising an anchor connectable between the sheet and part of a patient's body to inhibit diaphragmatic hernia of part of a stomach enclosed by the sheet.

9. The system of claim 7, wherein the sheet is formed of a natural tissue material.

10. The system of claim 9, wherein the body portion and the end portions extending therefrom further comprise a length of a natural tissue material.

11. The system of claim 10, wherein the natural tissue material further comprises a treated animal tissue.

12. The system of claim 1, wherein the elongated body portion and end portions extending therefrom form a first banding apparatus, the system further comprising a second banding apparatus, such that the first and second banding apparatus may be applied to spaced apart portions of a patient's stomach to inhibit expansion of such stomach portions and, in turn, help reduce food consumption of the patient.

13. A system to limit expansion of at least part of a stomach, comprising:
a pair of spaced apart and generally cylindrical end portions, a first of the end portion operative to circumscribe a part of the esophagus adjacent the stomach, the second end portion operative to circumscribe a part of the stomach so as to restrict the part of the stomach to a reduced diameter; and
a generally cylindrical web of a flexible biocompatible material extending between and connecting the first and second end portions, the web being expandable from a first volume to a second volume, which is greater than the first volume.

14. The system of claim 13, wherein the second end portion further comprises a gastric banding apparatus connected to an end of the web.

15. The system of claim 13, wherein the web comprises a plurality of apertures extending between opposed surfaces of the web, the apertures permitting expansion of the web to the second volume.

16. The system of claim 15, wherein the apertures further comprise elongated slots extending generally longitudinally between the ends of the web.

17. The system of claim 15, wherein part of web distal the second end portion defines the first end portion of the system, the first end portion being substantially free of the apertures.

18. The system of claim 13, further comprising an adjustable restriction apparatus operatively associated with the second end portion, the restriction apparatus being operable to selectively adjust the diameter of the second end portion.

19. The system of claim 18, wherein the restriction apparatus further comprises at least one suture having a length applied about the second end portion to form a purse string having end portions that extend from the second end portion through an elongated conduit, the conduit having a first end that engages the second end portion and a distal end spaced apart from the first end of the conduit, wherein the diameter of the second end portion may be modified by adjusting the length of the at least one suture extending from the first end of the conduit.

20. The system of claim 13, further comprising a length of a biocompatible material attached to and extending from the web and terminating in distal end, the distal end being connectable to part of the patient's body distal an esophageal hiatus of the patient so as to anchor the web and inhibit diaphragmatic hernia.

21. The system of claim 13, wherein each of the end portions and web are formed of a natural, biological material.

22. The system of claim 21, wherein each of the end portions and web are formed of an animal tissue material.

23. The system of claim 13, wherein each of the end portions and web are formed of the same type of material.

24. A system to help reduce food consumption when applied to part of a patient's stomach, comprising:
restriction means for, when applied around part of the patient's stomach, restricting the part of the stomach to a desired reduced diameter, the restriction means having elongated means extending from a central part thereof for securing the restriction means relative to itself to provide the desired reduced diameter.

25. The system of claim 24, further comprising means for, when applied around another part of the patient's stomach between the restriction means and an esophagus of the patient, limiting dilation of the another part of the patient's stomach to about a selected volume.

26. The system of claim 25, further comprising means for selectively reducing a diameter of the restriction means.

27. The system of claim 25 further comprising means for anchoring part of the dilation limiting means relative to part of the patient's body so as to inhibit diaphragmatic hernia.

28. A system to help reduce consumption of food in a patient, comprising:
banding means for reducing part of a stomach of the patient to a desired diameter; and
means for enclosing at least a substantial part of the patient's stomach extending from the banding means to a location adjacent an esophagus of the patient, the means for enclosing permitting expansion and contraction of the part of the patient's stomach between a first volume and a second volume, which is greater than the first volume.

29. The system of claim 28, further comprising means for anchoring part of the means for enclosing relative to an internal part of the patient's body so as to inhibit diaphragmatic hernia of the patient's stomach.

30. The system of claim 28, further comprising means for selectively adjusting a diameter of the banding means.

31. An implantable system to inhibit expansion of an anatomical object located within the system, comprising:
an elongated body portion of a flexible, biological tissue material having longitudinally spaced apart ends and side edges extending between the ends thereof, a slot extending a length through part of the body portion substantially transverse to a long axis of the body portion; and
first and second elongated end portions, each extending longitudinally from a respective end of the body portion, at least one of the elongated end portions being dimensioned and configured to facilitate insertion thereof into the slot;
whereby, upon insertion of one of the first and second ends into the slot and movement of the inserted end portion through the slot and securing the end portions relative to an intermediate portion of the system, a generally cylindrical member is formed that inhibits radial expansion of the system.

32. The system of claim 31, further comprising a sheet of a flexible biocompatible material having ends spaced apart from each other by a generally cylindrical sidewall extending between the ends of the sheet, a plurality of apertures extending through a substantial portion of the sheet at numerous spaced apart locations between the side edges of the sheet, the slots facilitating a limited amount of expansion of the sheet, one end of the sidewall being attached to and extending from a side edge of the body portion.

* * * * *